(12) United States Patent
Kircher et al.

(10) Patent No.: US 12,213,786 B2
(45) Date of Patent: Feb. 4, 2025

(54) OCULOMOTOR BASED DECEPTION DETECTION USING AUDIO MULTI-ISSUE COMPARISON TESTING

(71) Applicant: Converus, Inc., Lehi, UT (US)

(72) Inventors: John C. Kircher, Lehi, UT (US); Grant G. Parkinson, Lehi, UT (US); Benjamin C. Stout, Lehi, UT (US); Dan J. Woltz, Lehi, UT (US)

(73) Assignee: Converus, Inc., Lehi, UT (US)

( * ) Notice: Subject to any disclaimer, the term of this patent is extended or adjusted under 35 U.S.C. 154(b) by 533 days.

(21) Appl. No.: 17/336,639

(22) Filed: Jun. 2, 2021

(65) Prior Publication Data

US 2021/0369162 A1    Dec. 2, 2021

Related U.S. Application Data

(60) Provisional application No. 63/033,600, filed on Jun. 2, 2020.

(51) Int. Cl.
*A61B 5/16*  (2006.01)
*A61B 3/11*  (2006.01)
(Continued)

(52) U.S. Cl.
CPC .............. *A61B 5/163* (2017.08); *A61B 3/112* (2013.01); *A61B 3/113* (2013.01); *A61B 3/14* (2013.01); *A61B 5/164* (2013.01)

(58) Field of Classification Search
None
See application file for complete search history.

(56) References Cited

U.S. PATENT DOCUMENTS

| 5,150,969 A | 9/1992 | Goldberg et al. |
| 5,704,367 A | 1/1998 | Ishikawa et al. |

(Continued)

FOREIGN PATENT DOCUMENTS

CO    2019005899 A1 *  6/2019  ............... A61B 5/11

OTHER PUBLICATIONS

Cook et al., "Lyin' Eyes: Ocular-motor Measures of Reading Reveal Deception," (Sep. 2012), J Exp Psychol Appl.; 18(3): 301-313. (Year: 2012).*

(Continued)

*Primary Examiner* — Joel Lamprecht
*Assistant Examiner* — Ashish S Jasani
(74) *Attorney, Agent, or Firm* — Bretton L. Crockett; TechLaw Ventures, PLLC

(57) ABSTRACT

Automated audio multi-issue comparison test (AMCT) protocols for deception detection. In one exemplary embodiment, testing equipment that may include an eye tracking device, such as an infrared camera, computer, keyboard, mouse, chin rest, and audio output device (headphones or speaker) is used. A series of Agree and Disagree statements regarding issues of interest are presented to the examinee in an audio format as by text-to-speech narration. Each statement must include an introductory phrase, topic phrase and declaration phrase. As statements are presented, a neutral image is presented on a visual display, then replaced by an image prompting the examinee to provide a response when the statement concludes. The eye tracker measures and records eye movements during the test. At the conclusion, ocular-motor measures and test question responses are combined by means of a logistic regression equation to compute the probability of deception.

18 Claims, 8 Drawing Sheets

(51) Int. Cl.
    *A61B 3/113*     (2006.01)
    *A61B 3/14*     (2006.01)

(56) References Cited

U.S. PATENT DOCUMENTS

| | | | |
|---|---|---|---|
| 5,771,261 | A | 6/1998 | Anbar |
| 6,854,879 | B2 | 2/2005 | Pavlidis |
| 8,571,629 | B2 | 10/2013 | Faro et al. |
| 9,026,678 | B2 | 5/2015 | Tegreene et al. |
| 9,832,510 | B2 | 11/2017 | Tegreene et al. |
| 10,339,511 | B2 | 7/2019 | Aziz et al. |
| 10,743,806 | B2 | 8/2020 | Macknik et al. |
| 11,457,847 | B2 | 10/2022 | Palti-Wasserman et al. |
| 11,607,160 | B2 † | 3/2023 | Cuestas Rodriguez |
| 11,723,566 | B2 | 8/2023 | Palti-Wasserman |
| 11,864,895 | B2 | 1/2024 | Palti-Wasserman et al. |
| 2004/0143170 | A1 | 7/2004 | DuRousseau |
| 2007/0270659 | A1 | 11/2007 | Giegerich |
| 2009/0216092 | A1 | 8/2009 | Waldorf et al. |
| 2010/0324454 | A1 | 12/2010 | Kircher et al. |
| 2017/0000971 | A1 | 1/2017 | Shimuta |
| 2017/0039045 | A1 | 2/2017 | Abrahami et al. |
| 2017/0119296 | A1 | 5/2017 | Macknik et al. |
| 2018/0160959 | A1 | 6/2018 | Wilde et al. |
| 2019/0384392 | A1 | 12/2019 | Aimone et al. |
| 2020/0052906 | A1 | 2/2020 | Cahill |
| 2020/0060598 | A1 | 2/2020 | Palti-Wasserman |
| 2020/0138337 | A1 | 5/2020 | Choi et al. |
| 2020/0383621 | A1 | 12/2020 | Cuestas Rodriguez |
| 2020/0390328 | A1 † | 12/2020 | Toth |
| 2022/0087584 | A1 | 3/2022 | Kircher et al. |
| 2024/0293059 | A1 | 9/2024 | Kircher et al. |

OTHER PUBLICATIONS

EyeDetect (<https://youtu.be/XwCrhDpDKJg?si=8tZ0CsAhk3INK6WB>, (Mar. 2, 2016), retrieved on May 29, 2024. (Year: 2016).*

Converus (<https://web.archive.org/web/20190327234930/https://converus.com/lie-detection-methods-faqs/>, (Mar. 27, 2019), retrieved on May 29, 2024) (Year: 2019).*

\* cited by examiner
† cited by third party

OCULOMOTOR BASED DECEPTION DETECTION USING AUDIO MULTI-ISSUE COMPARISON TESTING

CROSS-REFERENCE TO RELATED APPLICATION

This application claims the benefit of U.S. Provisional Application No. 63/033,600, filed Jun. 2, 2020, which is incorporated herein by reference in its entirety, including but not limited to those portions that specifically appear hereinafter.

TECHNICAL FIELD

This invention relates to automated deception detection testing methods, systems, and protocols.

BACKGROUND

U.S. Publication Patent No. 2010/0324454, the contents of which are incorporated herein by reference, discloses rapid, automated methods for using oculomotor measures to determine whether a person is being truthful or deceitful. A commercial product embodying such methods was released under the brand name EyeDetect® and has proven successful in the marketplace. Computer implemented methods that use this type of oculomotor or other measurements of physiological response have typically relied on the presentation of material, including questions or statements, to an examinee (participant) as written text appearing on a screen, with the measurements of physiological responses recorded as the examinee reads and/or responds to the written material. As a result, tests have been limited in application to persons having a sufficient level of reading ability to comprehend questions or statements provided to allow meaningful data to be measured and recorded.

An automated deception detection testing protocol or system which utilizes oculomotor measures and does not require the examinee to read would be an improvement in the art. Such a testing method or system that removes examiner fatigue, corruption or bias from testing while adding standardization and objectivity in the testing process would be a further improvement in the art.

SUMMARY

The present disclosure is directed to automated audio multi-issue comparison test (AMCT) protocols for deception detection. In one exemplary embodiment, testing equipment that may include an eye tracking device, such as an infrared camera, computer, keyboard, mouse, and chin rest may be used. An audio output, such as noise-cancelling headphones may be included as a part of the testing equipment. A set of pre-test instructions may be provided to the examinee in an audio format, as by text-to-speech (TTS) software. One or more short practice sessions may be used to familiarize the examinee with the testing process.

For the test, a series of statements requiring an "Agree" or "Disagree" response regarding the target behaviors or issues of interest are presented to the examinee by TTS software. The statements must each include an introductory phrase, topic phrase and declaration phrase. In one embodiment, there may be up to four issues of interest, and the number of statements may be balanced between the issues of interest with an even number of Agree statements and Disagree statements.

As statements are presented, a neutral image is presented on a visual display, which is replaced by an image prompting the examinee to provide a response, such as a mouse click, when the statement concludes. Once the examinee provides a response, a confirming image may be displayed. During the test, the high-precision eye tracker measures and records eye behaviors such as pupil dilation, including when Agree and Disagree statements are presented and statement responses recorded. The response may be required within a set time period, and the system may pause the test and alert the examinee if the examinee looks away from the screen.

At the conclusion of the test, the ocular-motor measures and test question responses may be analyzed by means of a decision model based on a logistic regression equation to compute the probability of credibility or deception.

DESCRIPTION OF THE DRAWINGS

It will be appreciated by those of ordinary skill in the art that the various drawings are for illustrative purposes only. The nature of the present disclosure, as well as other embodiments in accordance with this disclosure, may be more clearly understood by reference to the following detailed description, to the appended claims, and to the several drawings.

DETAILED DESCRIPTION

The present disclosure relates to apparatus, systems and methods for computer implemented deception detection testing audio presentation of questions and statements to the test subject. It will be appreciated by those skilled in the art that the embodiments herein described, while illustrative, are not intended to so limit this disclosure or the scope of the appended claims. Those skilled in the art will also understand that various combinations or modifications of the embodiments presented herein can be made without departing from the scope of this disclosure. All such alternate embodiments are within the scope of the present disclosure.

The present disclosure includes systems for conducting the testing protocols discussed herein, as well as the computer implemented methods related to such protocols. It will be appreciated that in some exemplary embodiments, such systems may include testing equipment for presenting the tests to an examinee and capturing the oculomotor and other data for analysis. Such testing equipment may include an eye tracking device, such as an infrared camera, computer, keyboard, mouse, and chin rest may be used. An audio output, such as noise-cancelling headphones may also be included as a part of the testing equipment. A set of pre-test instructions may be provided to the examinee in an audio format, as by TTS software.

Figure 1:
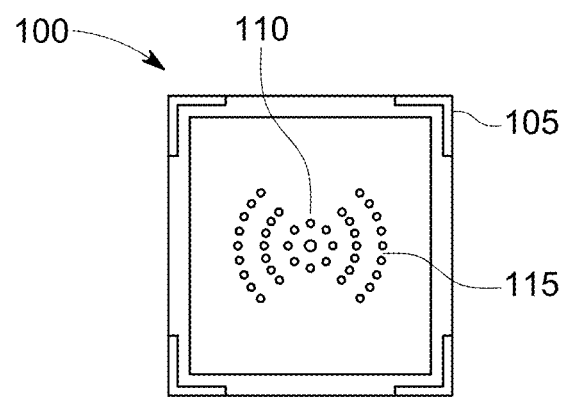
FIG. 1 is an example of an image that may be displayed on a visual display viewable to an examinee during testing in a testing protocol in accordance with the present disclosure, during the presentation of audio test instructions and/or the presentation of audio test statements.

One example of suitable testing equipment is the EyeDetect Station, which is commercially available from CONVERUS of Lehi, Utah. The primary hardware components of the EyeDetect Station include an eye tracking device (infrared camera), a Windows-based computer, keyboard, mouse, and chin rest. Noise-cancelling headphones (not shown) are also included. The eye tracker is a high definition, infrared camera that operates at 60 frames per second. Therefore, the eye tracker takes up to 60 measurements per second of the examinee's eyes. Changes as small as 1/10th of a millimeter are detected. During a test, hundreds of thousands of eye measurements may be recorded, as well as the examinee's responses to questions or statements. The eye tracker has a tracking range of 32×21 cm at a distance of 60 cm. It also has a +/−20° horizontal and +20°/−40° vertical range. During a test, eye measurements and test responses are temporarily stored on an encrypted drive on the EyeDetect Station. Suitable systems and operating environments may also include those disclosed in [0056]-[0074] and FIGS. 1a and 1b of US 2010/0324454, as discussed previously herein, which systems include an audio output that is accessible to an examinee.

Figure 6:
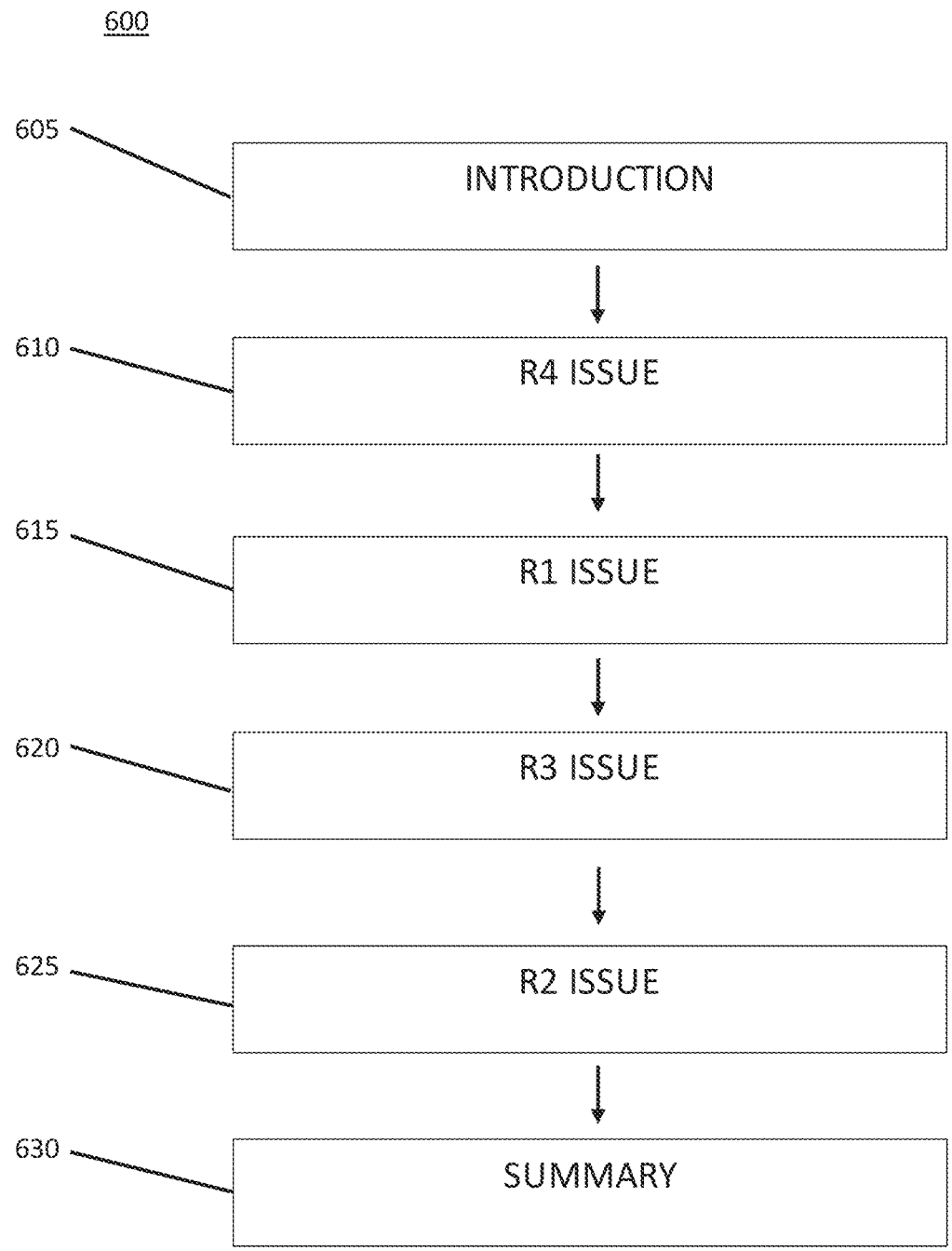
FIG. 6 is a template of a process or method that may be presented to an examinee during testing in a testing protocol in accordance with the present disclosure to aid in determining the credibility of the examinee.

The testing protocols in accordance with the present disclosure utilize the audio presentation of information on multiple issues of interest to an examinee to perform an audio multi-issue comparison test (AMCT). A typical AMCT protocol will perform testing on up to four relevant issues referred to in FIG. 6. Of these two or three relevant issues are of primary concern and the other relevant issue is used for comparison. The target behaviors or issues of interest may be designated Relevant Issue 1 or R1 (615), Relevant Issue 2 or R2 (620), Relevant Issue 3 or R3 (625) and Relevant Issue 4 or R4 (610) for purposes of this discussion. Typically, the R4 (610) is the most serious, the R1 (615) is the behavior with the highest probable failure rate, the R2 (620) is the second most probable issue to cause test failure, and the R3 (625) is the most serious of the R1-R3 (615, 620, 625). Each target behavior is treated independently of the others and is scored separately. For example, the each of relevant issues could address the examinee's participation in target behaviors or issues of concern for an employment position. In an illustrative example of a law enforcement preemployment test, R1 (615) could be illegal drug use, R2 (620) could be unreported work-related discipline, R3 (625) could be acts of crime, and R4 (610) could be a relevant issue with a lower prior probability of guilt, such as terrorism. It will be appreciated that these examples are merely illustrative and any type of target behavior, such as sexual assault, criminal history, drug use, stealing, association with known criminals, weapons trafficking, falsifying a police application, etc. may be examined. When considering the target behaviors to address with the test, it is important to be as specific as possible to eliminate any uncertainty for the examinee. R4 (610) should meet the following criteria: 1) be a crime more serious than the other relevant issues. 2) not cross over with the other relevant issues (should not be a related topic), 3) have face validity for the examinee (i.e., the examinee must believe the issue is important), and 4) have an expected prior probability of guilt of <3%.

In order to conduct an AMCT test, an examinee is placed in front of the testing equipment such that they can view the display and be tracked by the eye tracker, as by placing the examinee's chin on a chin rest (where present). A set of pre-test instructions may then be provided to the examinee in an audio format, as by TTS software. The pre-test instructions may discuss the images to be shown onscreen and instruct the examinee how to respond. One or more short practice sessions may then be used to familiarize the examinee with the testing process.

The pre-test instructions may also introduce and summarize the relevant issues on which the examinee will be assessed. An exemplary set of instructions is presented as FIG. 6 for a law enforcement pre-employment test template 600. Then instructions including introduction 605 begin with a short introduction, and briefly present the issues in the order of R4 (610), R1 (615), R2 (620), and R3 (625), followed by summary 630 that is very similar to introduction 605.

An exemplary test may include the following introduction and summary:

Introduction 605: This pre-employment credibility assessment test for the Metro Police Department will ask about your involvement in these four issues <ssml><break time="500 ms"/></ssml> Ties to foreign or domestic terrorist organizations, Use of illegal drugs, Unreported work-related discipline, and Commission of a crime act.

R4 issue: First, the Metro Police Department wants to ensure that none of its employees have personally been involved with a foreign or domestic terrorist organization. Involvement implies that you have worked with, have supported, or have provided information to further their activities. Examples include organizations such as <ssml><break time="500 ms"/></ssml> ISIS, Al-Qaeda, the Taliban, Hamas, or any other terrorist organization.

Terrorists create unrest by attacking law enforcement, military personnel, innocent civilians, and the nation's infrastructure. These organizations have a religious or political agenda with the goal of destroying democratic systems of government or simply creating terror. In the United States, association with terrorist organizations is a serious offense and is punishable by up to 60 years in prison.

R1 issue 615: Second, this test will ask about your use of illegal drugs. Specifically, Metro Police Department wants to know if you have used, bought, possessed or sold illegal drugs, within the past 5 years. Examples include <ssml><break time="500 ms"/></ssml> Cocaine, Heroin, Crack, Ecstasy, LSD, PCP, Meth, or any other similar "hard" drugs. The question about illegal drug use also applies to the use of marijuana or synthetic marijuana in the past 12 months.

R2 issue 620: Third, this test will ask if you have withheld or falsified any information about your previous work-related discipline. This means that you chose to conceal, hide some facts, or not report past work-related discipline. This could include lying about <ssml><break time="500 ms"/></ssml> getting fired, forced resignation, demotion, discharge, suspension, written reprimand, investigation, or any other action taken by a previous employer for cause.

R3 Issue 623 Lastly, this test will ask if you have committed a crime act, as an adult. Crime acts include criminal acts against a person or against property, that could result in your arrest, conviction, and a prison sentence. This includes any crime acts committed as an adult, whether you were caught or not caught. This test is not concerned with crimes you committed as a minor.

Examples of crime acts could include <ssml><break time="500 ms"/></ssml> Robbery, which is to take property from another person by force. Burglary, which is to enter a building or vehicle illegally. Assault, which is to physically attack someone. Domestic violence, which includes physical or mental abuse of a spouse or partner. Sexual assault or rape. Sexual abuse of a minor, which is physical sexual contact as an adult with someone under 16 years of age. Or, Possession or distribution of child pornography. Accepting or receiving bribes, such as money or gifts, for doing something improper. Being a part of gangs or organized crime. Or, any other serious crime.

In summary 630, this test will ask about your involvement in these four issues <ssml><break time="500 ms"/></ssml> Ties to foreign or domestic terrorist organizations, Use of illegal drugs, Unreported work-related discipline, and Commission of a crime act.

If you have ties with foreign or domestic terrorists, have used or possessed illegal drugs within the designated time frames, have lied about previous work-related discipline, or have committed a crime act as an adult, please tell the test administrator now.

Following the introduction and summary, the test may proceed. For the test, a series of Agree and Disagree statements regarding the issues of interest are presented to the examinee by TTS software. The use of TTS software provides a neutral presentation of the instructions and statements. The Agree/Disagree statements should be provided to the system in textual form that is then "read" to the examinee using TTS software. The statements should include any required accommodations such that they sound natural when read to the examinee. For example, commas that introduce a short pause in narration should be provided, including after each item in a list. (Ex: Cocaine, Heroin, Crack, Ecstasy, LSD, Meth, or other similar "hard" drugs). In some embodiments, use of the HTML code <ssml><break time="500 ms"></ssml> introduces a half second pause. This code may be used before a list of examples. (Ex: Examples of terrorists include <ssml><break time="500 ms"></ssml> ISIS, Al-Qaeda, the Taliban, Hamas, or, any other terrorist organizations).

In one embodiment, there may be up to four issues of interest, and the number of statements may be balanced between the issues of interest and with an even number of statements to which Agree/Disagree responses are expected. Typically, there are 2 or 3 relevant issues (R1, R2, and R3) and a comparison issue (R4). There is typically an even number of iterations or versions of each relevant statement. Half require an "Agree" response and half require a "Disagree" response, in order to maintain balance in the examinee's responses. In the illustrative example, there are eight iterations for each relevant issue, with four requiring an "Agree" response and four requiring a "Disagree" response. Each statement is written in a way to cause the examinee to have to wait until she or he hears the entire statement before responding.

The relevant statements should be structured to invoke a thoughtful response in the examinee. Each should be unique, with no identical statements. The average length of the relevant statements should be similar. Each relevant statement should include an introductory phrase, topic phrase and a declaration phrase.

Introductory phrases are lead-in phrases to the topic. These include phrases such as: As to; With regard to; Concerning; About the; Speaking of; With respect to; Regarding; and In reference to.

Topic phrases identify the topic and combine introductory phrases with the specific topic (shown below in bold text). Examples include:
  As to the money reported missing, I took it.
  Regarding sexual contact with that girl, I am responsible.
  Concerning the use of illegal drugs, I am guilty.
  Speaking of document falsification, I am innocent.

Declaration phrases include the decision points, which are the phrases to which the examinee responds. These are binary statements that can only be answered Agree or Disagree. They are written in first person. Examples include:
  I am innocent.
  I am guilty.
  I am responsible.
  I did not take it.
  I admit doing it.
  I did not do it.
  I am the one that stole it.
  I did not steal it.
  I was not involved.

Relevant phrases should vary within a topic—but may be similar between topics. For example, there should be eight unique phrases for R1, but the pattern of introductory and declaration phrases may be similar in R2. For example (shown in bold and italics below):
  R1: About the cash reported missing, I did not take it.
  R1: Regarding the cash reported missing, I did not steal it.
  R2: About the use of illegal drugs, I have not participated.
  R2: Regarding the use of illegal drugs, I am responsible.

Figure 2:
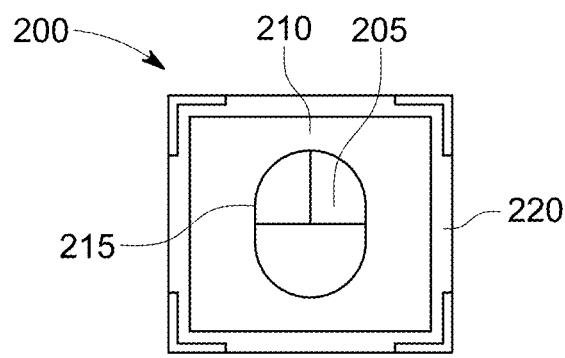
FIG. 2 is an example of an image that may be displayed on a visual display viewable to an examinee during testing in a testing protocol in accordance with the present disclosure when the presentation of an audio test statement has concluded and a response may be provided.
Figure 3A:
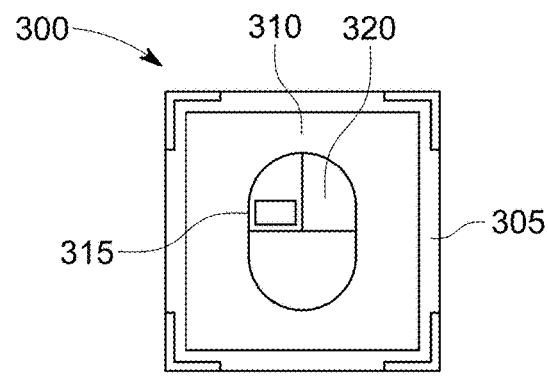
FIGS. 3A and 3B are examples of images that may be displayed on a visual display viewable to an examinee during testing in a testing protocol in accordance with the present disclosure to confirm that a response to a presented audio test statement has been recorded.
Figure 3B:
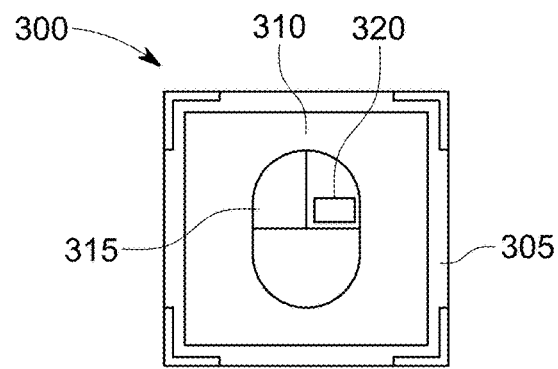

As statements are presented by being read by the TTS software, a neutral image is presented on a visual display. One example of a neutral image 100 is present in FIG. 1 and provides a point on the display on which the examinee can focus to aid in the tracking of eye movement. Neutral image 100 may include framing 105 and icon 110. Icon 110 may include a series of dots 115. Dots 115 may flash change colors rotate or remain stationary in a manner that provides a focal point for the examinee. When a statement concludes, image 100 is replaced by prompting image 200 prompting the examinee to provide a response, such as a mouse click. FIG. 2 provides an example of prompting image 200. Prompting image 200 may include framing 205 and icon 210. Icon 210 may be a symbol of a computer mouse with three sections including left mouse button 215 right mouse button 220 and a hand rest portion of the icon. Icon 210 may be flashing or may move within the frame 205 to draw the attention of the examinee. Alternatively, icon 210 may remain motionless. Once the examinee provides a response, confirming image 300 may be displayed. FIGS. 3A and 3B depict examples of such confirming images 300. Confirming images 300 may include frame 305 and icon 310 wherein icon 310 in this embodiment represents a computer mouse. Further icon 310 may be used to indicate an "Agree" and "Disagree" response corresponding to the selection of left mouse button 315 or right mouse button 320 as a response to one or more statements or questions. In response to a selection, left mouse button 315 may include a green square indicating that the examinee elected to agree by pressing the left mouse button. Alternatively, if the examinee chooses to disagree by clicking the right mouse butt right mouse button 320 may include a red square within the icon 310. By highlighting the button chosen by the examinee this may act as a conformation that the computer received the answer chosen by the examinee.

The high-precision eye tracker measures and records eye movements during the test, including as the statements are presented and the responses received. The information gathered by the eye tracker during a test may include: (1) Measurements of the X and Y coordinates of gaze position, pupil diameter, and (2) The examinee's agree/disagree responses to the test questions.

It will be appreciated that the oculomotor data are not photographs, are not biometrics, and cannot be used to identify any person. Further, where an organization wishes to protect the identity of any examinee for purposes of reporting testing results, during registration prior to taking a test, the test examiner can provide an identifying number rather than the examinee's name for tracking test results.

Figure 4:
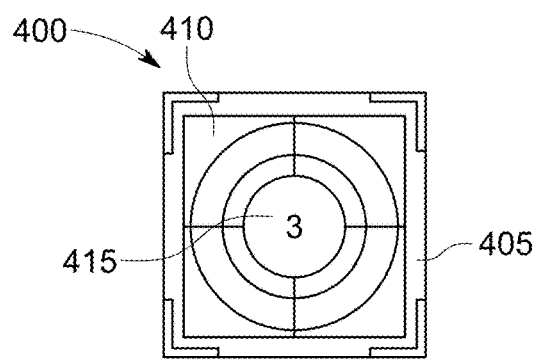
FIG. 4 is an example of an image that may be displayed on a visual display viewable to an examinee during testing in a testing protocol in accordance with the present disclosure to indicate that the time to respond to a presented audio test statement has expired.

The system may pause the test and alert the examinee if the examinee looks away from the screen during the test; such an alert may include an audio portion and a display image 400 as depicted in FIG. 4. Display image 400 may include frame 405 and icon 410 with number indicator 415. Number indicator 415 may be located at the center of icon 410 these numbers may decrease or increase indicating either the amount of time the examinee took his eyes from the screen or the amount of time left before the examinee fails to maintain proper eye contact for the test. Number indicator 415 may include color that changes the longer the examinee looks away. Further, number indicator 415 may flash as the examinee approaches failure due to lack of focus on the screen.

Figure 5:
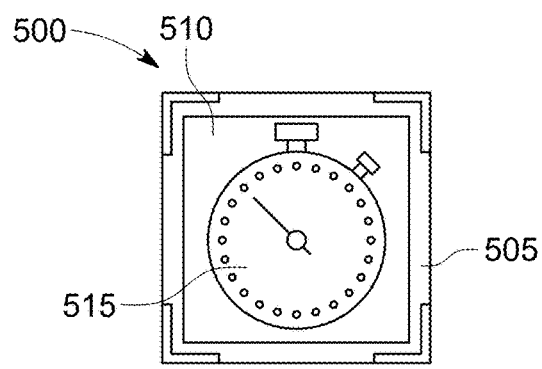
FIG. 5 is an example of an image that may be displayed on a visual display viewable to an examinee during testing in a testing protocol in accordance with the present disclosure to indicate that the examinee has looked away from the screen.

Each response may be required within a set time period, after which the examinee may be informed that the time to respond has passed, including by displaying an image 510, such as that depicted in FIG. 5. To extract the best reaction in the event the examinee is deceptive, examinees must respond quickly. Examinees that intentionally delay in responding, those that respond randomly, or those that attempt to use countermeasures are considered non-cooperative and will be given a Not Credible score in the test. Image 500 including frame 505 with icon 510 may be used to invite compliance to answer the questions within the time frame. Icon 510 may include a stopwatch 515 to show that time is running out. Stopwatch 515 may show up to indicate a delay. As the delay continues stopwatch 515 may flash or change colors as the examinee approaches a set time limit to be considered non-cooperative.

It will be appreciated that instructions and relevant statements may be presented in any language that is understood by the examinee, so long as a TTS voice is available for such language, or there are audio recordings of test instructions and statements in the test subject's native language.

At the conclusion of the test, the ocular-motor measures and test question responses may be combined by means of a logistic regression equation to compute the probability of deception. In some embodiments, this may be performed by the testing equipment. In the typical embodiment however, the data taken in each test is encrypted and securely stored on the testing equipment computer, which it then synchronized with a secure web server that is part of the system.

As mentioned above, the credibility score may be a logistic regression equation, which is a statistical method for analyzing a data set with one or more independent variables. Such a logistic regression equation may be represented as:

$$Pr(\text{Deceptive}) = 1/(1 + \exp(b0 + b1X1 + b2X2 + \ldots + bkXk))$$

where $X1 \ldots Xk$ represents one or more ocular-motor characteristics and where $b0 \ldots bk$ an optimal weight associated with the one or more ocular-motor characteristics. If $Pr(\text{Deceptive}) < 0.50$, then the credibility score is rated "deceptive." If $Pr(\text{Deceptive}) > 0.50$, then the credibility score is rated "truthful." The resulting calculation yields a binary outcome. With the AMCT, the binary outcome is represented as two possible outcomes: 1) truthful or 2) deceptive. Some of the independent variables considered in the algorithm include pupil dilation, response accuracy, response time, blink rate, and gaze fixations, among others. The aim of the equation is to obtain an answer that is reasonable and measurable and that will accurately describe the relationship between the test subject's deceptive status and the set of independent variables considered—pupil dilation, precision of the response, gaze, response time, fixation, etc. For the AMCT, the logistic regression equation chooses independent variables that maximize the accuracy of the classifications of deception or credibility. The result is a credibility score. The Credibility Score represents the probability of belonging to the "Credible" group. A higher score means it is more probable that the score came from the Innocent distribution. Scores from 50 to 99 are considered Credible and scores from 1 to 49 are considered Not Credible. The closer the Credibility score is to 1, the greater the probability of deception, where the probability of deception is determined as an inverse percentage of the Credibility score. On the contrary, the closer to 99, the more likely it is the person is telling the truth. Scores of 50 and greater may be considered "passing" scores and scores between 0 and 49 may be considered "failing" scores. Essentially, a score of 51 is as good as a score of 99. This is because the decision model (algorithm) establishes "50" at the point where errors are balanced. It will be appreciated that different values for determining the Credible/Not Credible boundary may be used for particular applications.

Figure 7:
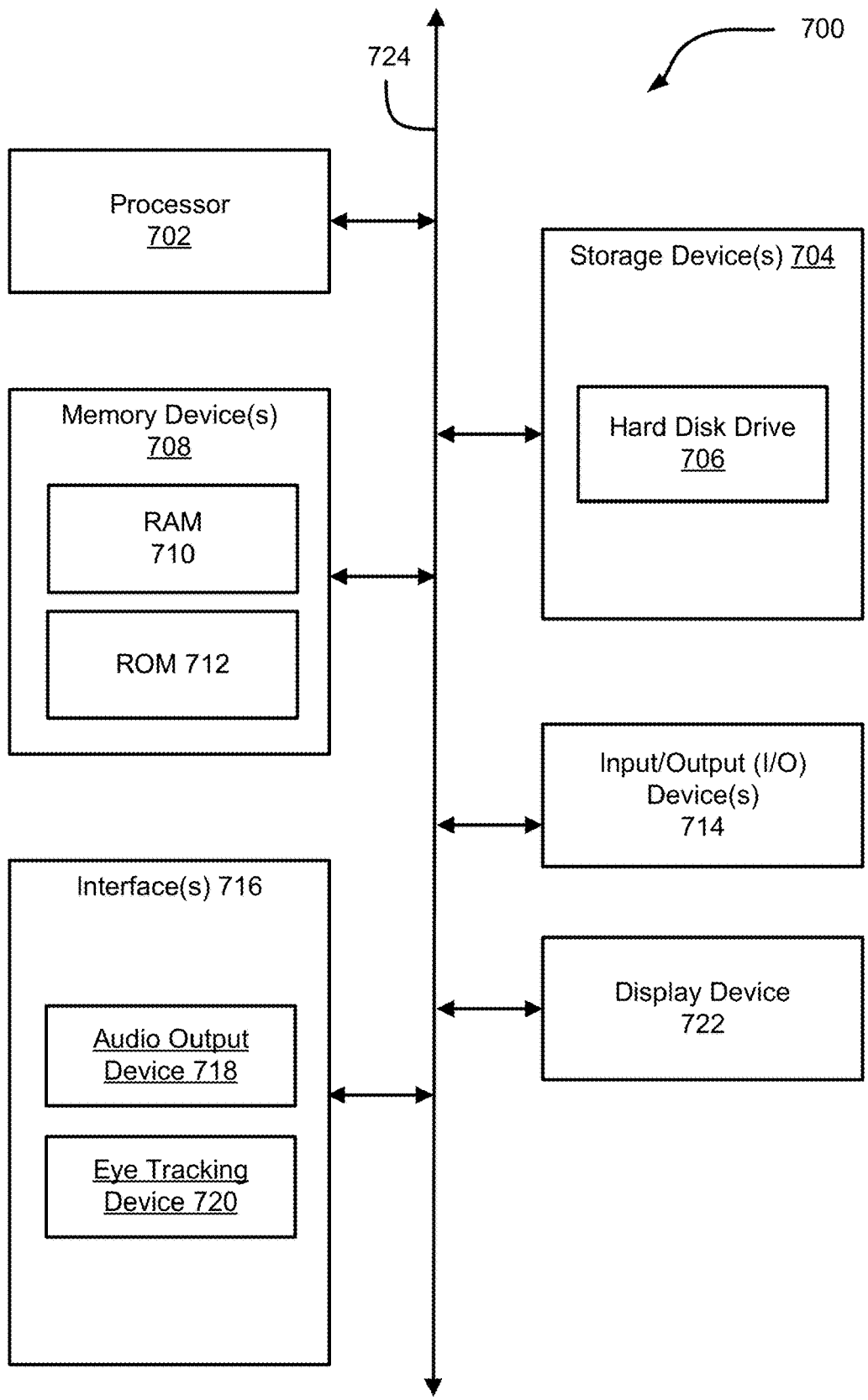
FIG. 7 is an exemplary hardware configuration of a system for credibility assessment according to the principles of the present disclosure.

FIG. 7 shows an exemplary hardware configuration of a system 700 for credibility analysis according to the principles of the present disclosure. The system may include a processor 702 for executing software instructions in electronic communication with various other hardware components of the system. Hardware components may include storage devices 704 including but not limited to one or more hard disk drives 706. Hardware components may further include memory devices 708, including but not limited to RAM memory 710 and/or ROM memory 712. Hardware components may further include input/output devices 714 including but not limited to a computer mouse or keyboard for a user to interact with the system 700. Hardware components may further include more specific interfaces 716, such as audio output device 718 or eye tracking device 720 for transmitting or receiving hardware-specific information to or from a user. Hardware components may additionally include a display device 722 for displaying information to a user. The listing of hardware components recited herein is not exhaustive, and it will be appreciated by those skilled in the art that hardware systems may include more or less hardware components according to the configuration.

Figure 8A:
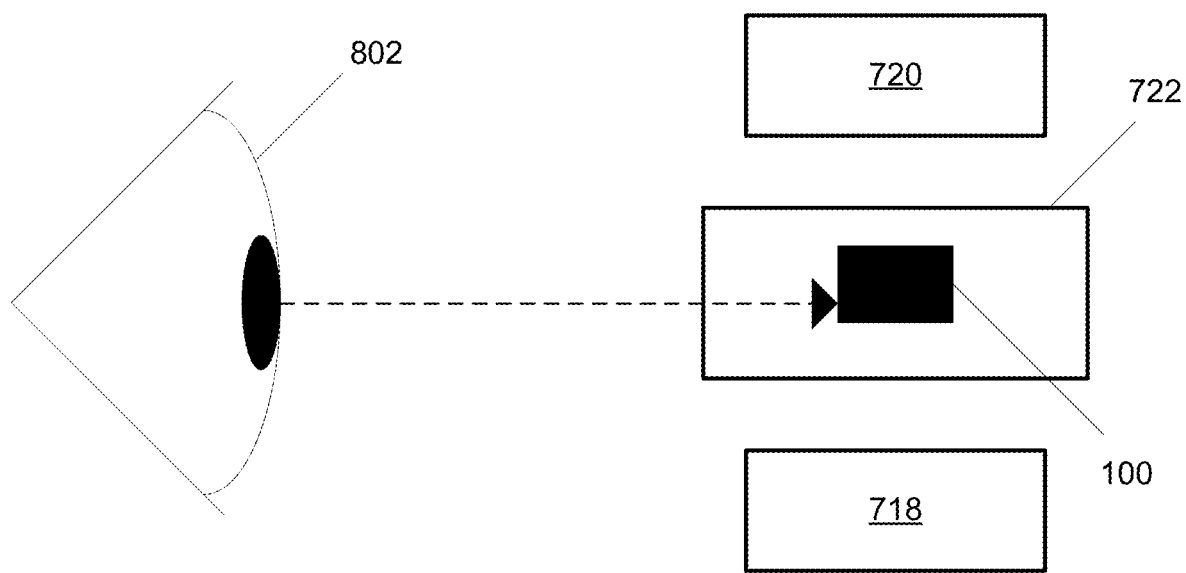
FIG. 8A is a schematic diagram of a test taker observing a neutral image for testing purposes according to the principles of the present disclosure.
Figure 8B:
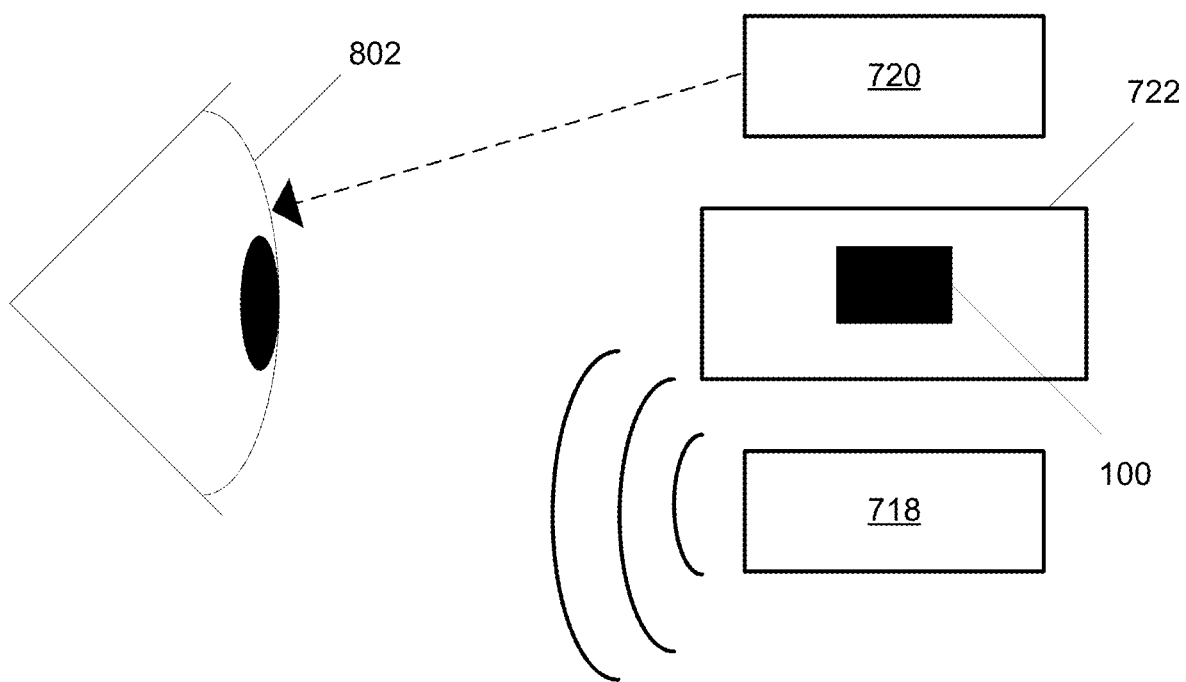
FIG. 8B is a schematic diagram of a system delivering a test question to a test taker according to the principles of the present disclosure.

FIG. 8A shows a schematic diagram of a test taker observing a neutral image for testing purposes according to the principles of the present disclosure. When engaged in a testing protocol, a user 802 may interact with a system as shown in FIG. 7. The system may include, depending on the implementation, an eye tracking device 720, an audio output device 718, and a display device 722. During testing, a user may observe a neutral image 100 as described in FIG. 1. The user may focus on the neutral image to aid in the tracking of eye movement. Once calibrated, the system may, via the audio output device 718, provide a test question to test taker 802, as shown in FIG. 8B. While providing the question, the system may observe and track test taker 802 eye activity via the eye tracking device 720.

Figure 8C:
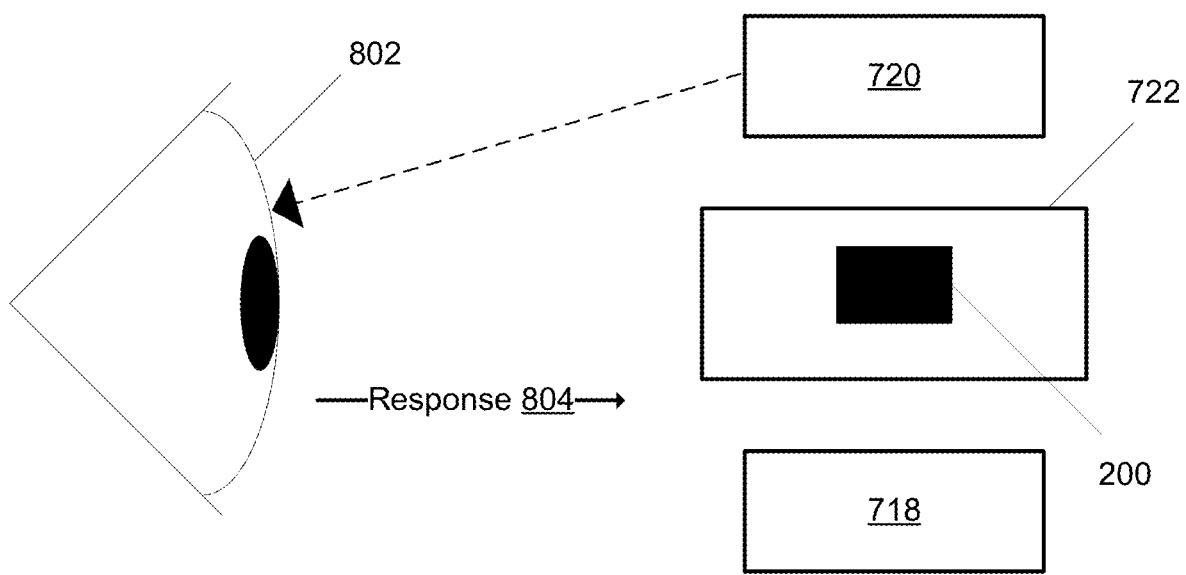
FIG. 8C is a schematic diagram of a system observing oculomotor behavior of a test taker while the test taker provides a response according to the principles of the present disclosure.

FIG. 8C shows a schematic diagram of the system observing a test taker 802. Once the audio output device 718 finishes delivering the test question, the display device 722 may then display a prompting image 200 as discussed in FIG. 2 and accompanying disclosure thereof. The test taker 802 may then provide a response 804 to the test question. In some implementations, the response 804 may be delivered via hardware such as a mouse click. It will be appreciated by those of ordinary skill in the art that the system may collect different forms of responses from a test taker 802 by any suitable means. As the test taker 802 listens to the test question and provides a response 804, the eye tracking device 720 may continue to monitor eye activity of the test taker 802. At any point during testing, if the eye tracking device 722 is unable to observe the test taker 802's eyes, the system may update the display device 722 to display an alert image as discussed in FIG. 4 and accompany disclosure and may or may not further produce an audio alert via the audio output device 718.

Figure 8D:
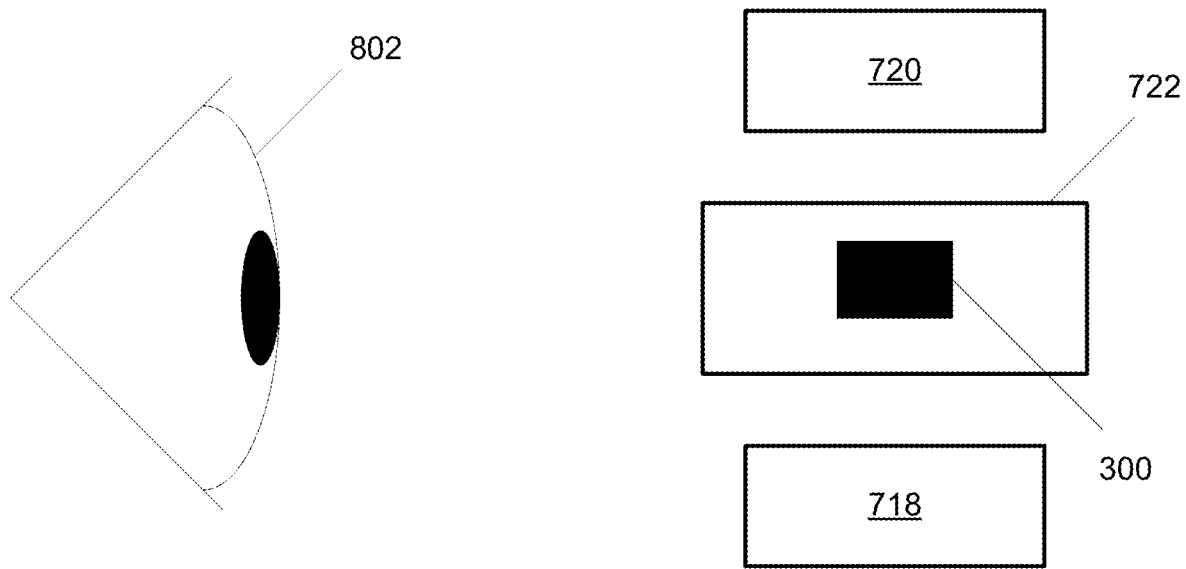
FIG. 8D is a schematic diagram of a test system displaying a confirming image after receiving a response form the test taker for testing purposes according to the principles of the present disclosure.

Once the system receives the response 804, the system may update the display device 722 to show a confirmation image 300, to indicate the response 804 was received, as shown in FIG. 8D. The response may then be processed as part of a determination of credibility for the test taker 802, as discussed within this disclosure.

EXPERIMENT

A mock crime experiment was conducted which was modeled after Cook et al. (Cook, A. E., Hacker, D. J., Webb, A. K., Osher, D., Kristjansson, S., Woltz, D. J., & Kircher, J. C. (2012). Lyin' Eyes: Ocular-motor Measures of Reading Reveal Deception. Journal of Experimental Psychology: Applied, 18(3), 301-313), the contents of which are incorporated herein by reference. The experiment was conducted to collect the ocular-motor data needed to develop and cross-validate a statistical model of ocular-motor measures that computes a credibility score for each issue. In this experiment, there were four issues: (1) theft of cash, (2) theft of a gift card, (3) theft of a cell phone, and (4) theft of a headlamp.

One hundred and eighty (180) subjects were recruited from the local community. They were told some subjects would commit one or more of the thefts, whereas others would be innocent and would not commit any of the crimes. Subjects were arbitrarily assigned to one of three groups. One of two groups of guilty subjects stole $20 from a secretary (n=74). The other group of guilty subjects stole $20 from a secretary AND stole a gift card from a wallet (n=55). The third group of subjects was innocent of all four crimes (n=51).

After subjects completed their instructions, they were given a credibility test in accordance with the present disclosure and designated as the AMCT. The AMCT contained eight True/False statements about each of the four topics (32 items) and the set of 32 items was repeated five times in different orders. A TTS voice presented instructions and test statements orally over headphones while an eye tracker (Tobii brand) recorded gaze position and pupil size of left and right eyes. The computer also recorded response times and the number of questions answered incorrectly. Subjects were told they should respond quickly and accurately to the statements or they would fail the test. Subjects were paid for their time and were paid an additional $30 bonus if they passed the test.

Analysis

Ocular-motor data were analyzed to identify features that discriminated between questions answered truthfully and deceptively. A set of ocular-motor features was identified that achieved better than 80% accuracy on the complete set of relevant questions. For each subject, those features were weighed and combined by means of a logistic regression equation that generated a credibility score for each relevant question. The credibility index was the probability that the person was truthful about that topic. If the credibility index was 0.5 or greater, the subject was classified as truthful to questions about that issue. If the credibility index was less than 0.5, the subject was classified as deceptive about that issue.

A statistical model that is optimal for classifying the cases in a particular experiment is rarely optimal for the population from which the subjects were sampled. The model is not optimal because the sample does not perfectly represent the more general population from which it was drawn. Consequently, we obtain biased estimates of accuracy if we test the model on the cases that were used to create the model.

Better estimates of accuracy can be obtained with k-fold validation. A k-fold validation divides the data set into k folds (subsets). The first subset comprises a hold-out subsample and is removed from the dataset. The remaining subsets are combined to create a training set. A logistic regression model is developed using the cases in the training set. That logistic regression model is then used to classify the cases in the hold-out subsample. The accuracy observed in the hold-out sample provides a less biased estimate of accuracy because the holdout cases were not used to optimize feature coefficients in the regression equation. The accuracy achieved in the hold-out sample is recorded.

This process continues for each partition of the data set. The first subset is returned to the training set, and the second subset is removed to serve as a new holdout sample. A new logistic regression model is created with all but the second subset of cases. That model is used to classify cases in the holdout sample, and its accuracy is recorded. This process is repeated for each of the remaining subsets. The best estimate of accuracy for the model is mean accuracy across the k holdout samples.

One hundred and eighty (180) subjects were available to validate the AMCT. Each subject was truthful or deceptive to each of four relevant questions. That provided a total of 180×4=720 relevant questions where the person was truthful or deceptive. K-fold validation was completed with 296 of those 720 relevant questions. To achieve a proper balance of truthful and deceptive cases and deceptive answers by guilty subjects who committed one or two crimes, the number of questions for the validation process was limited by the number of guilty subjects who committed one crime (n=74). All 74 of the questions answered deceptively were included in the validation sample. Then, an equal number of deceptive questions was obtained from a random sample of 37 of the 55 guilty subjects who committed two crimes. Each of those 37 guilty subjects contributed two cases to the deceptive validation sample (2×37=74) because they lied to two of the four questions on the test. Since the validation sample now contained 2×74=148 deceptive cases, an equal number of questions truthfully was randomly selected from the entire sample of 180 subjects. That subsample of 148 truthful cases contained a random mix of questions answered truthfully by people who were truthful to all relevant questions (innocent) or were truthful to some questions but not others (guilty).

An 8-fold validation was performed. The sample of 296 questions was split into 8 subsamples of either 36 or 38 questions. Half of the questions in each subsample were questions answered truthfully, and half were questions answered deceptively. Half of the questions answered deceptively were from subjects who committed one crime and half were from subjects who committed two crimes. Table 1 shows percent correct for truthful and deceptive questions for each fold, as well as the mean accuracy across the eight folds.

TABLE 1

|  | Fold 1 | Fold 2 | Fold 3 | Fold 4 | Fold 5 | Fold 6 | Fold 7 | Fold 8 | Mean |
|---|---|---|---|---|---|---|---|---|---|
|  |  |  |  |  | n |  |  |  |  |
|  | 36 | 38 | 36 | 38 | 36 | 38 | 36 | 38 | 296 (total n) |
| Truthful | 88.9 | 89.5 | 83.3 | 84.2 | 77.8 | 78.9 | 66.7 | 84.2 | 81.7 |
| Deceptive | 88.9 | 89.5 | 55.6 | 78.9 | 83.3 | 73.7 | 83.3 | 84.2 | 79.7 |
|  |  |  |  |  |  |  |  | Mean Accuracy | 80.7 |

On average, accuracy was slightly higher for questions answered truthfully (81.7%) than for questions answered deceptively (79.7%). At the level of individual relevant questions, mean accuracy on cross validation was 80.7%. Based on these results, we would expect the AMCT to produce 80.7% correct decisions when the model is used in a new sample.

A new logistic regression equation was developed using all 720 questions from the 180 subjects. The observed mean accuracy at the level of individual questions was 82.2%. When the model was used to decide whether a subject was deceptive to any one or more of the relevant questions, its mean accuracy was 80.7%. The model is slightly more accurate for deceptive subjects (83.1%) than for truthful subjects (78.4%).

While this disclosure has been described using certain embodiments, it can be further modified while keeping within its spirit and scope. This application is therefore intended to cover any variations, uses, or adaptations of the disclosure using its general principles. This application is intended to cover any and all such departures from the present disclosure as come within known or customary practices in the art to which it pertains, and which fall within the limits of the appended claims.

What is claimed is:

1. A system for credibility analysis including:
   a processor, the processor presenting to a subject one or more statements or questions, as part of a credibility assessment test, prompting a response from the subject, wherein the one or more statements or questions presented by the processor includes a topic phrase and a declaration phrase;
   an eye tracking device connected to the processor comprising:
      an infrared camera configured to track one or more oculomotor activities of the subject during the credibility assessment test;
   an audio output device in electronic communication with the processor configured to transmit the one or more statements or questions as sound to the subject;
   a display screen connected to the processor presenting to the subject one or more images during the presentation of the one or more statements or questions, wherein at least a portion of the one or more images comprises a neutral image;
   wherein the neutral image is an icon serving as a focal point for the subject;
   wherein the infrared camera measures the one or more oculomotor activities when the neutral image is displayed and the subject observes the neutral image, and wherein the audio output device transmits the one or more statements or questions while the subject observes the neutral image;
   wherein the processor analyzes the response received from the subject and compares the response to an expected response;
   wherein the processor calculates a credibility score based on the measured one or more oculomotor activities and assess the response comparison to determine whether the subject is credible or not credible.

2. The system for credibility analysis of claim 1, wherein the neutral image is subsequently replaced by a prompting image after the audio output device transmits the one or more statements or questions, and
   wherein the prompting image is subsequently replaced by a confirming image after the system receives the response from the subject.

3. The system for credibility analysis of claim 1, wherein in the one or more oculomotor activities tracked by the eye-tracking device comprises one or more of:
   a pupil dilation of the subject,
   a gaze position of the subject,
   a gaze fixation of the subject,
   a fixation time of the gaze fixation of the subject, or
   a blink rate of the subject.

4. The system for credibility analysis of claim 1, wherein the response comparison comprises one or more of a response time of the subject, a response accuracy of the subject, or a response precision of the subject.

5. The system for credibility analysis of claim 1, wherein the one or more statements or questions presented by the processor further includes an introductory phrase.

6. The system for credibility analysis of claim 1, wherein the one or more statements or questions presented by the process are focused on target behavior or issues about the subject.

7. A process for credibility analysis comprising:
- transmitting, by one or more processors, one or more statements or questions to a subject, as part of a credibility test, prompting a response from the subject;
- transmitting, by the one or more processors, one or more images to a display screen in view of the subject, wherein at least a portion of the one or more images comprises a neutral image;
- wherein the neutral image is an icon serving as a focal point for the subject;
- transmitting, by the one or more processors, one or more of the one or more statements or questions aurally to the subject by an audio output device in electrical communication with the one or more processors;
- receiving, by the one or more processors, one or more responses from the subject to the one or more statements or questions and comparing the one or more responses from the subject to an expected one or more responses;
- receiving, by the one or more processors, one or more oculomotor activities of the subject from an eye tracking device comprising an infrared camera, wherein at least a portion of the one or more oculomotor activities are measured while the audio output device transmits the one or more statements or questions to the subject and while the subject observes the neutral image;
- calculating, by the one or more processors, a credibility score based on the measured one or more oculomotor activities;
- determining, based on the credibility score and the response comparison, whether the subject is credible or not credible.

8. The process for credibility analysis of claim 7, wherein the neutral image is subsequently replaced by a prompting image after the audio output device transmits the one or more statements or questions, and
wherein the prompting image is subsequently replaced by a confirming image after the system receives the response from the subject.

9. The process for credibility analysis of claim 7, wherein in the oculomotor activity tracked by the eye-tracking device comprises one or more of:
- a pupil dilation of the subject,
- a gaze position of the subject,
- a gaze fixation of the subject,
- a fixation time of the gaze fixation of the subject, or
- a blink rate of the subject.

10. The process for credibility analysis of claim 7, wherein the response comparison comprises one or more of a response time of the subject, a response accuracy of the subject, or a response precision of the subject.

11. The process for credibility analysis of claim 7, the one or more statements or questions presented by the processor includes an introductory phrase.

12. The process for credibility analysis of claim 11, wherein the one or more statements or questions presented by the processor include a topic phrase.

13. The process for credibility analysis of claim 12, wherein the one or more statements or questions presented by the processor include a declaration phrase.

14. The process for credibility analysis of claim 1, wherein the one or more statements or questions presented by the process are focused on target behavior or issues about the subject.

15. The system for credibility analysis of claim 1, wherein the processor is further configured to calculate a probability of deception score based on the credibility score.

16. The system of credibility analysis of claim 1, wherein the processor is further configured to produce an alert when the eye tracking device cannot detect oculomotor activity of the subject, and wherein the alert comprises one or both of an audio alert generated by the audio output device or a visual alert image displayed on the display.

17. The process for credibility analysis of claim 7, the steps further comprising calculating a probability of deception score based on the credibility score.

18. The process for credibility analysis of claim 7, the steps further comprising producing an alert when the eye tracking device cannot detect oculomotor activity of the subject, and wherein the alert comprises one or both of an audio alert generated by the audio output device or a visual alert image displayed on the display.

* * * * *